(12) United States Patent
Breslich et al.

(10) Patent No.: US 11,096,699 B2
(45) Date of Patent: Aug. 24, 2021

(54) DRILL GUIDE ASSEMBLY

(71) Applicant: CONMED CORPORATION, Utica, NY (US)

(72) Inventors: Grady Breslich, Bradenton, FL (US); Trey Smith, Tampa, FL (US)

(73) Assignee: CONMED CORPORATION, Utica, NY (US)

( * ) Notice: Subject to any disclaimer, the term of this patent is extended or adjusted under 35 U.S.C. 154(b) by 231 days.

(21) Appl. No.: 16/460,384

(22) Filed: Jul. 2, 2019

(65) Prior Publication Data
US 2020/0008819 A1    Jan. 9, 2020

Related U.S. Application Data

(60) Provisional application No. 62/693,776, filed on Jul. 3, 2018.

(51) Int. Cl.
| | |
|---|---|
| *A61B 17/17* | (2006.01) |
| *A61B 17/70* | (2006.01) |
| *A61B 17/88* | (2006.01) |
| *A61B 17/00* | (2006.01) |

(52) U.S. Cl.
CPC ...... *A61B 17/1796* (2013.01); *A61B 17/7082* (2013.01); *A61B 17/8875* (2013.01); *A61B 17/8894* (2013.01); *A61B 2017/0046* (2013.01)

(58) Field of Classification Search
CPC ............ A61B 17/1796; A61B 17/8875; A61B 17/7082; A61B 17/8894
See application file for complete search history.

(56) References Cited

U.S. PATENT DOCUMENTS

| | | | |
|---|---|---|---|
| 2006/0100627 A1* | 5/2006 | Stone | A61F 2/0811 |
| | | | 424/426 |
| 2018/0111740 A1* | 4/2018 | Marantis | A61M 1/0003 |
| 2018/0214190 A1* | 8/2018 | Erramilli | A61B 17/7082 |

FOREIGN PATENT DOCUMENTS

JP         3889777 B1 *  3/2007  ............ A61F 2/0811

* cited by examiner

*Primary Examiner* — Christian A Sevilla
(74) *Attorney, Agent, or Firm* — Bond, Schoeneck & King, PLLC; Frederick J. M. Price (57) ABSTRACT

A drill guide to facilitate drilling a hole into a bone and inserting an anchor. The drill guide includes a handle extending to a proximal end and a guide shaft extending from the handle to a distal end. A recess extends into the handle at the proximal end. The drill guide also includes a channel extending through the recess and into the guide shaft and a contact surface extending from the recess. The contact surface may be a proximal surface on a ring extending circumferentially within the recess. The contact surface may alternatively be a proximal surface on a protrusion extending from and within the recess. For example, the protrusion is a triangular protrusion extending along the recess toward the channel. The contact surface allows for the use of inserters of varying sizes within the channel of the drill guide.

2 Claims, 15 Drawing Sheets

DRILL GUIDE ASSEMBLY

CROSS-REFERENCE TO RELATED APPLICATIONS

This application claims priority to U.S. Provisional Patent Application Ser. No. 62/693,776, filed on Jul. 3, 2018 and entitled "Guide with Improved Instrument Insertion and Depth Control Features," the entirety of which is incorporated herein by reference.

BACKGROUND OF THE INVENTION

1. Field of the Invention

The present invention is directed generally to a surgical system and, more particularly, to a drill guide to facilitate drilling a hole into a bone and inserting an anchor.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone. In such surgeries, prior to insertion of a suture anchor, a pilot hole is drilled into the bone. Traditionally, a standard single barrel drill guide is placed at the desired pilot hole location on the bone and a drill is placed through the drill guide to create the pilot hole. The drill is then removed and replaced with a driver (or "inserter") pre-loaded with the suture anchor.

Standard single barrel drill guides may have a flat, uniform (i.e., even) contact surface where the drill enters the drill guide. As a result of the flat contact surface, only instruments of one size can be accommodated in the drill guide. A drill guide able to accommodate drills and inserters of multiple sizes can be used for numerous procedures, thereby requiring fewer instruments and decreasing the number of steps for carrying out the procedure.

Therefore, there is a need for a compact drill guide with one or more contact surfaces for accommodating instruments of varying sizes.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a drill guide for facilitating drilling a hole into a bone and inserting an anchor. According to one aspect, the present invention is a drill guide extending along a longitudinal axis with a proximal end and a distal end, and includes a handle extending to the proximal end and a guide shaft extending from the distal end of the handle to the distal end of the drill guide. A recess extends into the handle at the proximal end. The drill guide also includes a channel extending through the recess and into the guide shaft and a contact surface extending from the recess. The contact surface may be a proximal surface on a ring extending circumferentially within the recess. The contact surface may alternatively be a proximal surface on a protrusion extending from and within the recess. For example, the protrusion is a triangular protrusion extending along the recess toward the channel.

According to another aspect, the drill guide extending along a longitudinal axis with a proximal end and a distal end, and includes a handle extending to the proximal end and a guide shaft extending from the distal end of the handle to a distal end of the drill guide. A recess extends into the handle at the proximal end. The drill guide also includes a channel extending through the recess and into the guide shaft, and a plurality of protrusions extending from the recess. Each protrusion has a proximal contact surface.

According to another aspect, the drill guide extending along a longitudinal axis with a proximal end and a distal end, and includes a handle extending to the proximal end and a guide shaft extending from the distal end of the handle to a distal end of the drill guide. A recess extends into the handle at the proximal end. The drill guide also includes a channel extending through the recess and into the guide shaft, and a plurality of rings extending circumferentially within the recess and from an exterior surface of the recess. Each of the plurality of rings has a proximal contact surface.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
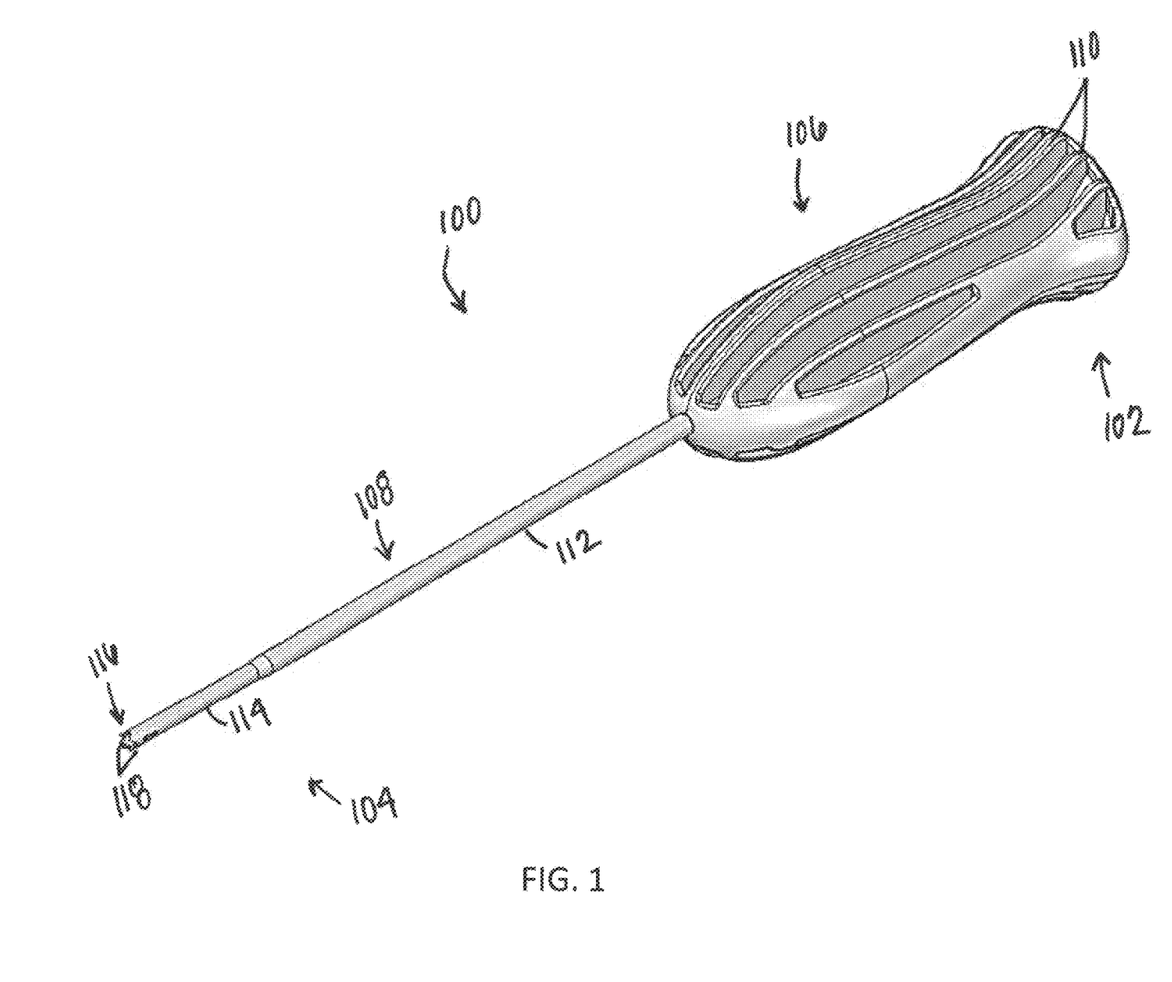
FIG. 1 is a perspective view schematic representation of a drill guide, according to an embodiment.

Referring now to the figures, wherein like reference numerals refer to like parts throughout, FIG. 1 shows a perspective view schematic representation of a drill guide 100, according to an embodiment. The drill guide 100 comprises a proximal end 102 and a distal end 104. The proximal end 102 comprises a handle 106 extending to a cannulated guide shaft 108. In some embodiments, the guide shaft 108 extends proximally through the handle 106. The guide shaft 108 extends distally to the distal end 104 of the drill guide 100. In the embodiment shown in FIG. 1, the handle 106 is ergonomically curved for a comfortable grip. Further, the handle 106 of the drill guide 100 in FIG. 1 comprises a plurality of ridges 110 for a better grip for the user.

Still referring to FIG. 1, as stated above, the guide shaft 108 extends distally from the handle 106. In the depicted embodiment, the guide shaft 108 is narrow, having a diameter smaller than a diameter of the handle 106. As shown in FIG. 1, the guide shaft 108 has a first portion 112 and a second portion 114. The first portion 112 is connected to and between the second portion 114 and the handle 106. In the depicted embodiment, the second portion 114 has a diameter which is smaller than a diameter of the first portion 112; however, varying combinations of diameters or a uniform diameter of the guide shaft 108 may be used. At a minimum, the guide shaft 108 must have a diameter wide enough to pass a drill and an anchor therethrough. As shown in FIG. 1, the second portion 114 comprises a distal crown end 116. The distal crown end 116 comprises a plurality of protrusions 118 extending distally from the second portion 114. The protrusions 118 engage the bone at the surgical site and can aid in stabilizing the drill guide 100.

Figure 2:
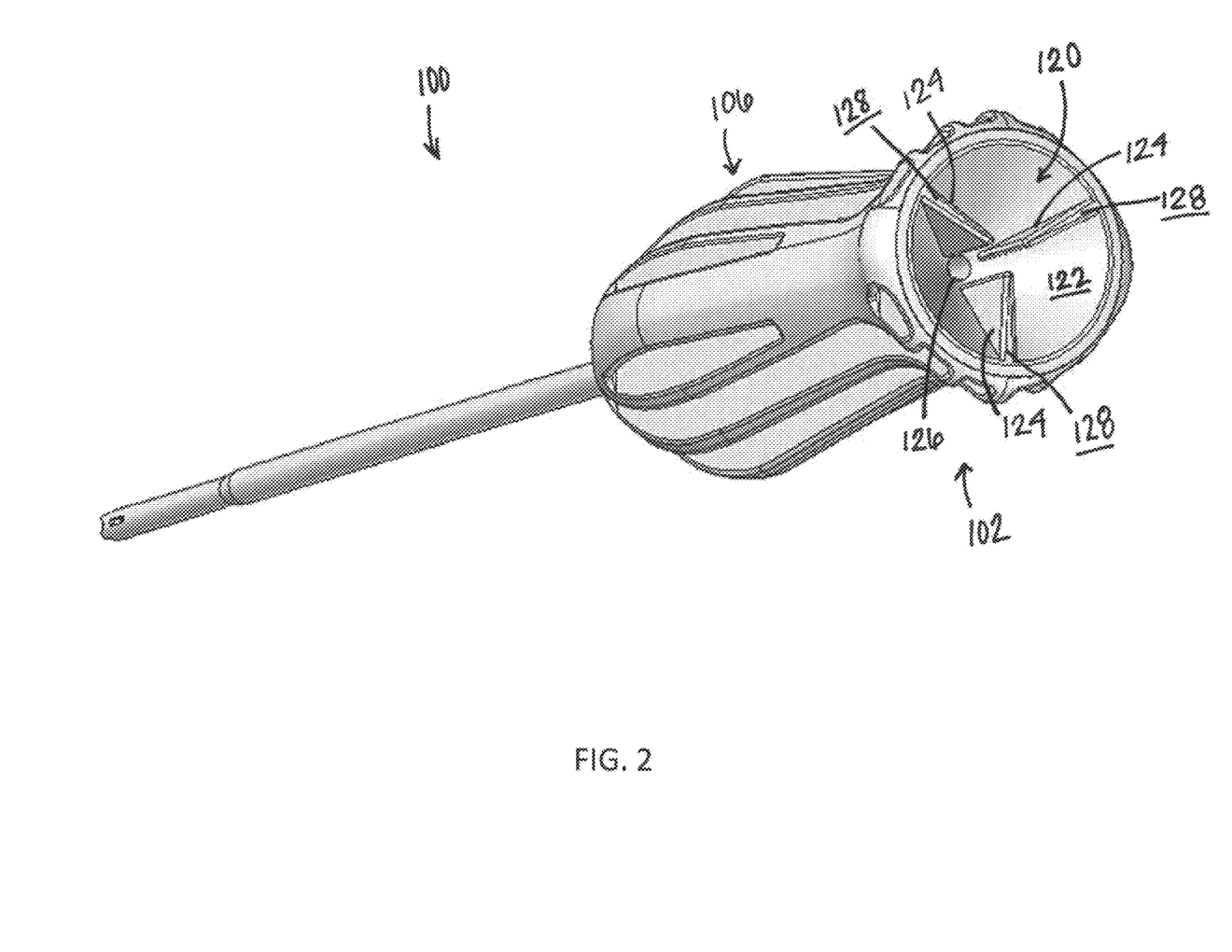
FIG. 2 is another perspective view schematic representation of the drill guide, according to an embodiment.

Turning now to FIG. 2, there is shown another perspective view schematic representation of the drill guide 100. As shown, the proximal end 102 of the drill guide 100 comprises a recess 120 (or cavity) extending into the handle 106. In the depicted embodiment, the recess 120 is funnel-shaped, tapering distally. The recess 120 comprises an exterior surface 122 with one or more fins 124 protruding therefrom. In the depicted embodiment, the fins 124 are triangular projections that extend radially toward a central channel 126 in the recess 120. Each fin 124 comprises a proximal contact surface 128 where an inserter 200 (FIGS. 12-15) extending through the channel 126 will contact the drill guide 100. In the depicted embodiment, the contact surface 128 of each fin 124 is the proximalmost surface of the fin 124.

Figure 3:
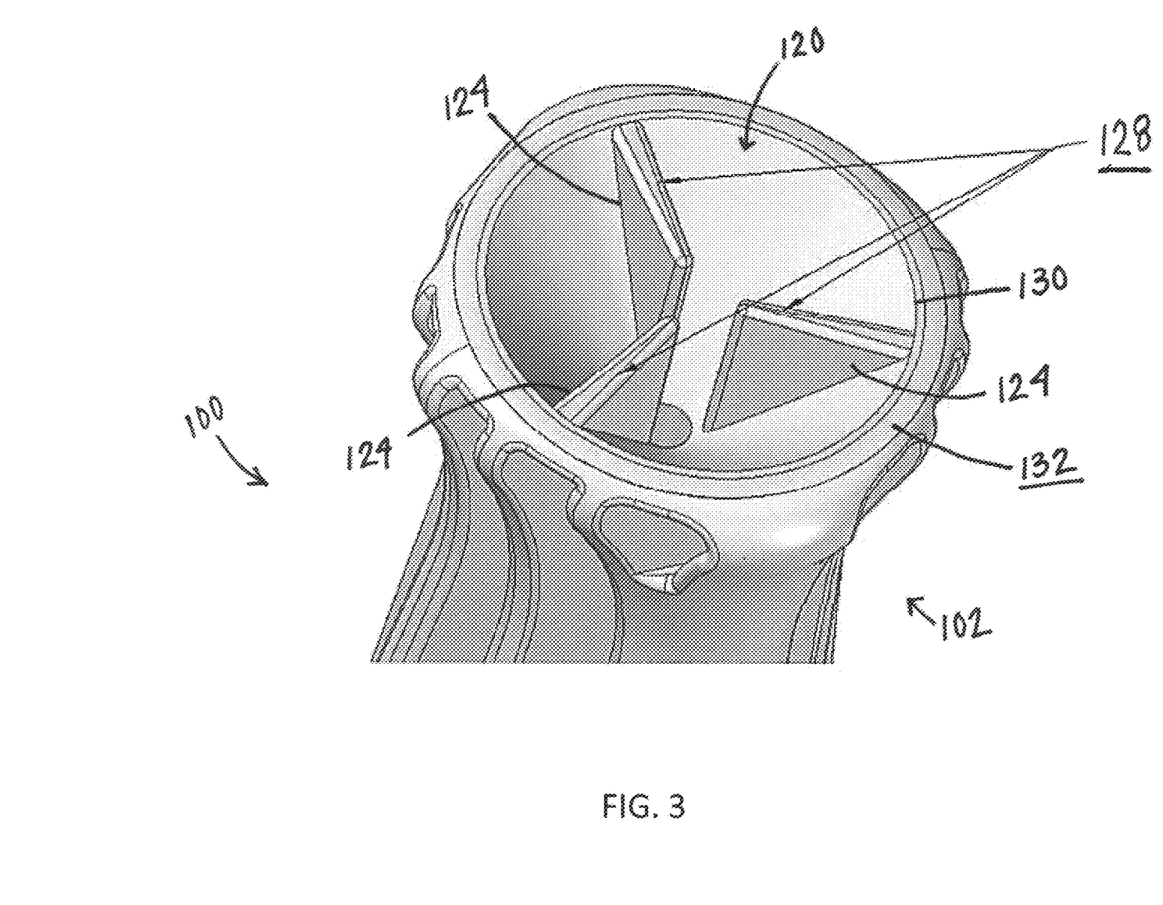
FIG. 3 is a close-up perspective view schematic representation of the proximal end of the drill guide, according to an embodiment.
Figure 4:
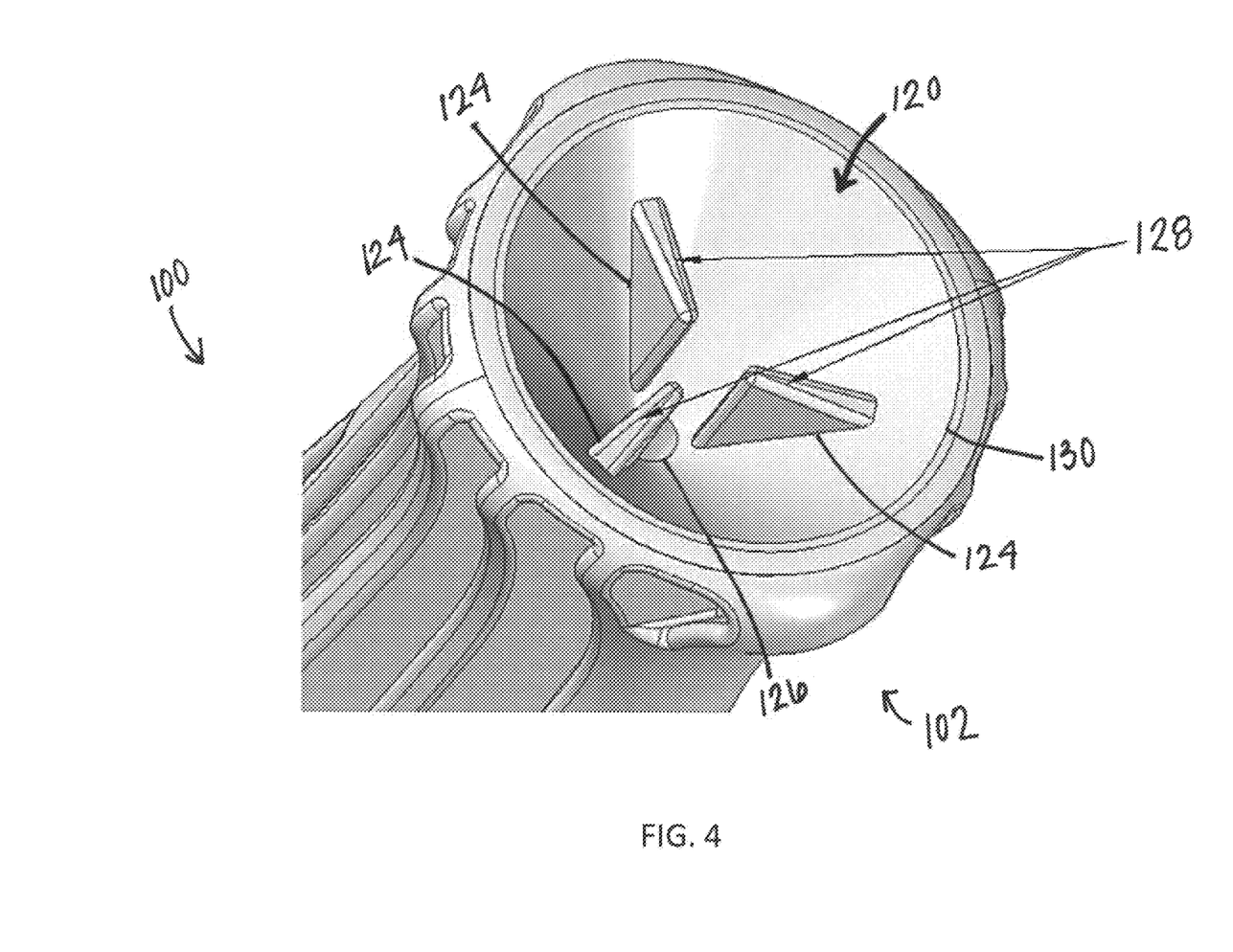
FIG. 4 is a close-up perspective view schematic representation of the proximal end of the drill guide, according to an alternative embodiment.
Figure 5:
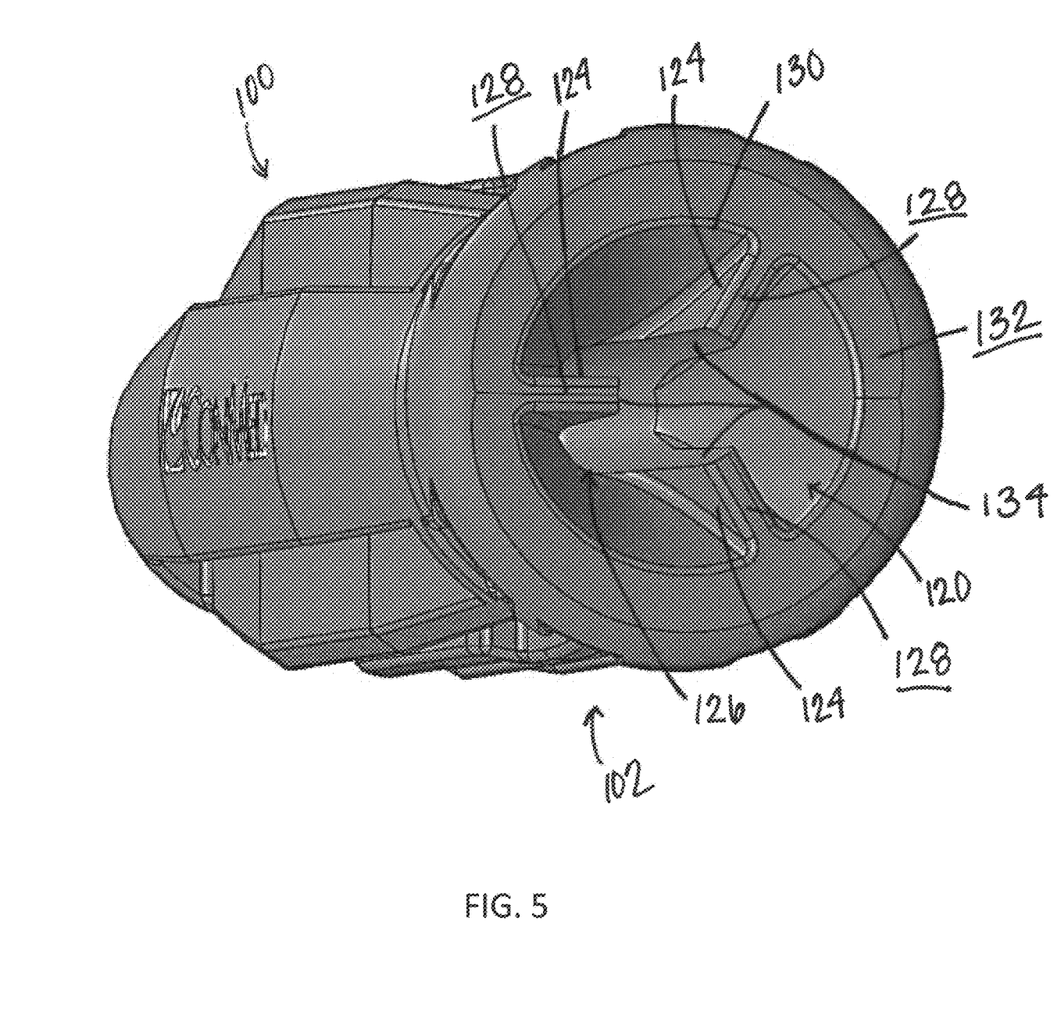
FIG. 5 is a perspective view schematic representation of the proximal end of the drill guide, according to another embodiment.
Figure 6:
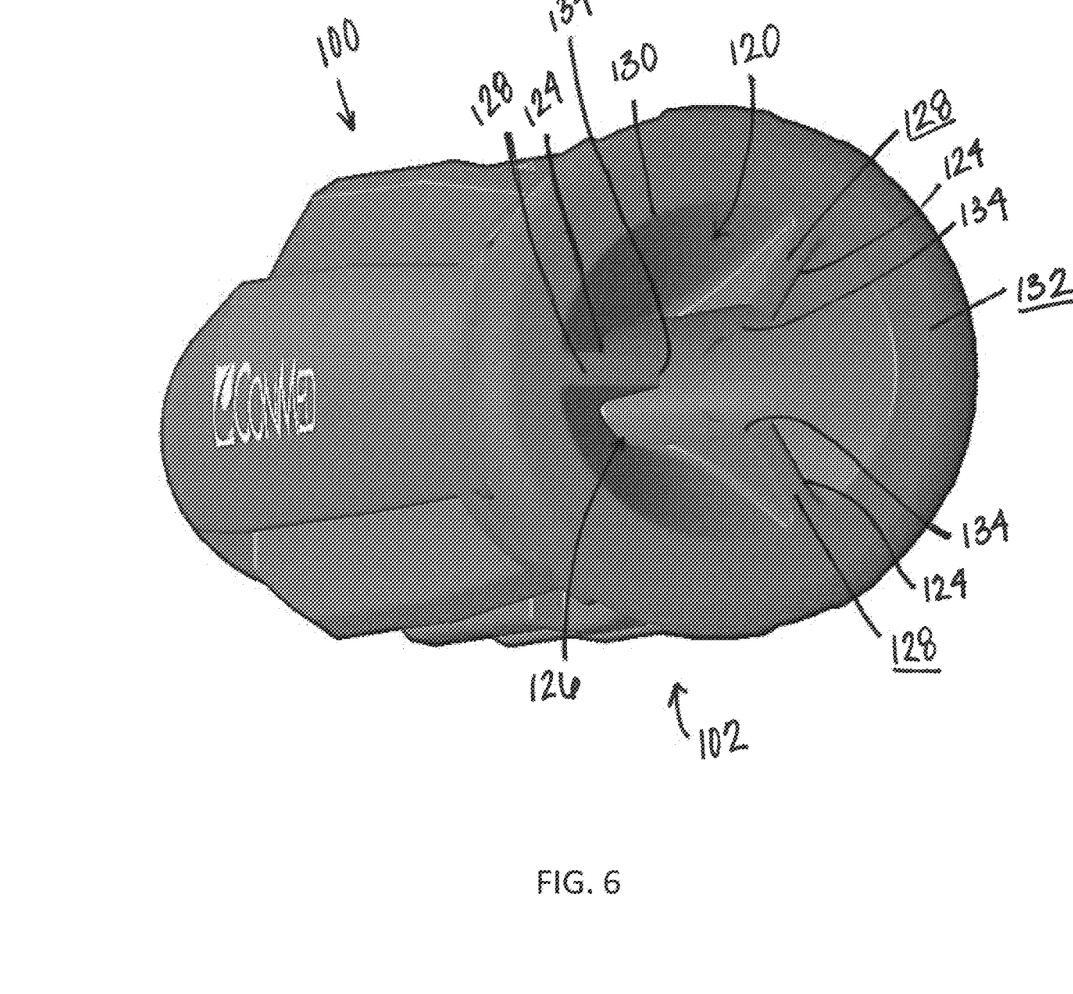
FIG. 6 is another perspective view schematic representation of the proximal end of the drill guide of FIG. 5.
Figure 7:
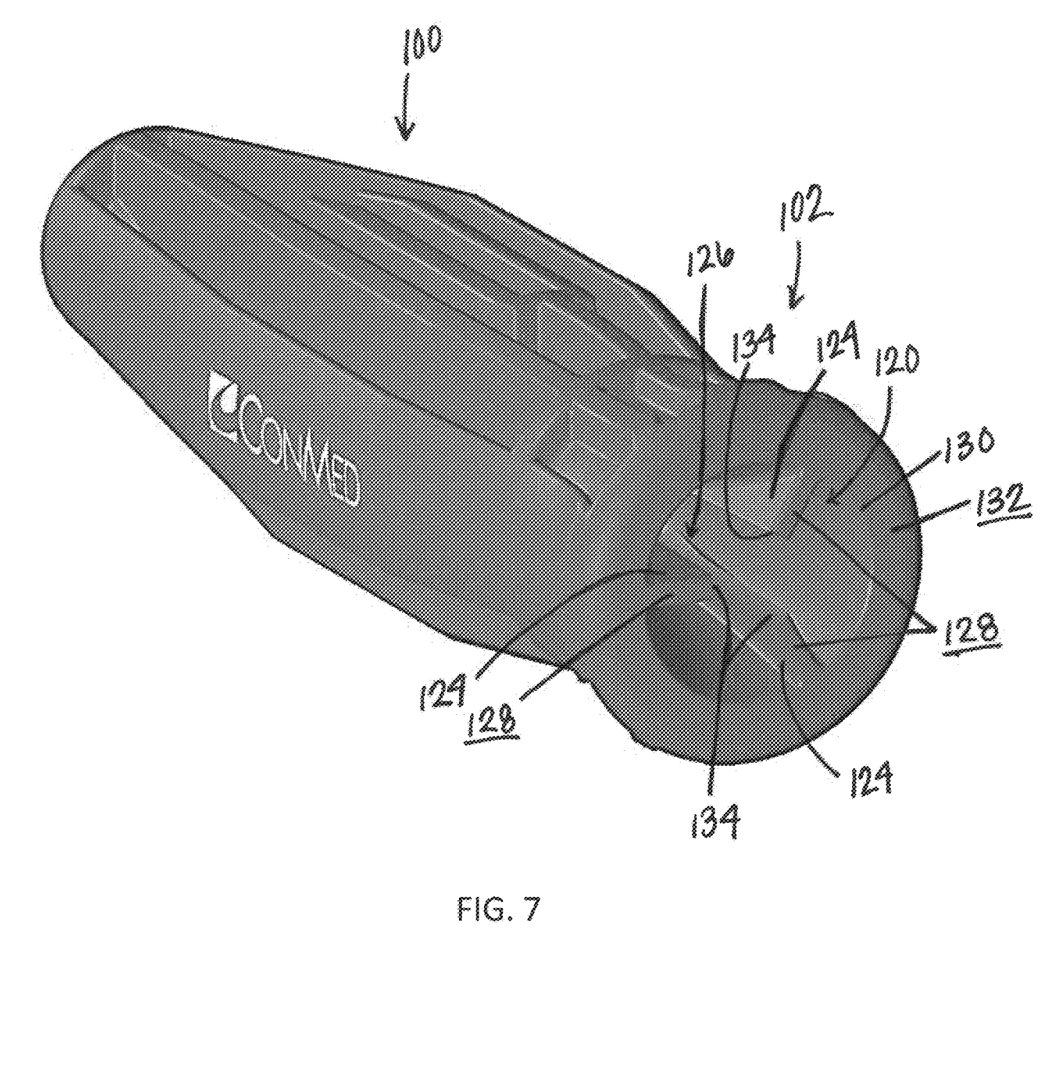
FIG. 7 is a perspective view schematic representation of the drill guide of FIG. 6.
Figure 8:
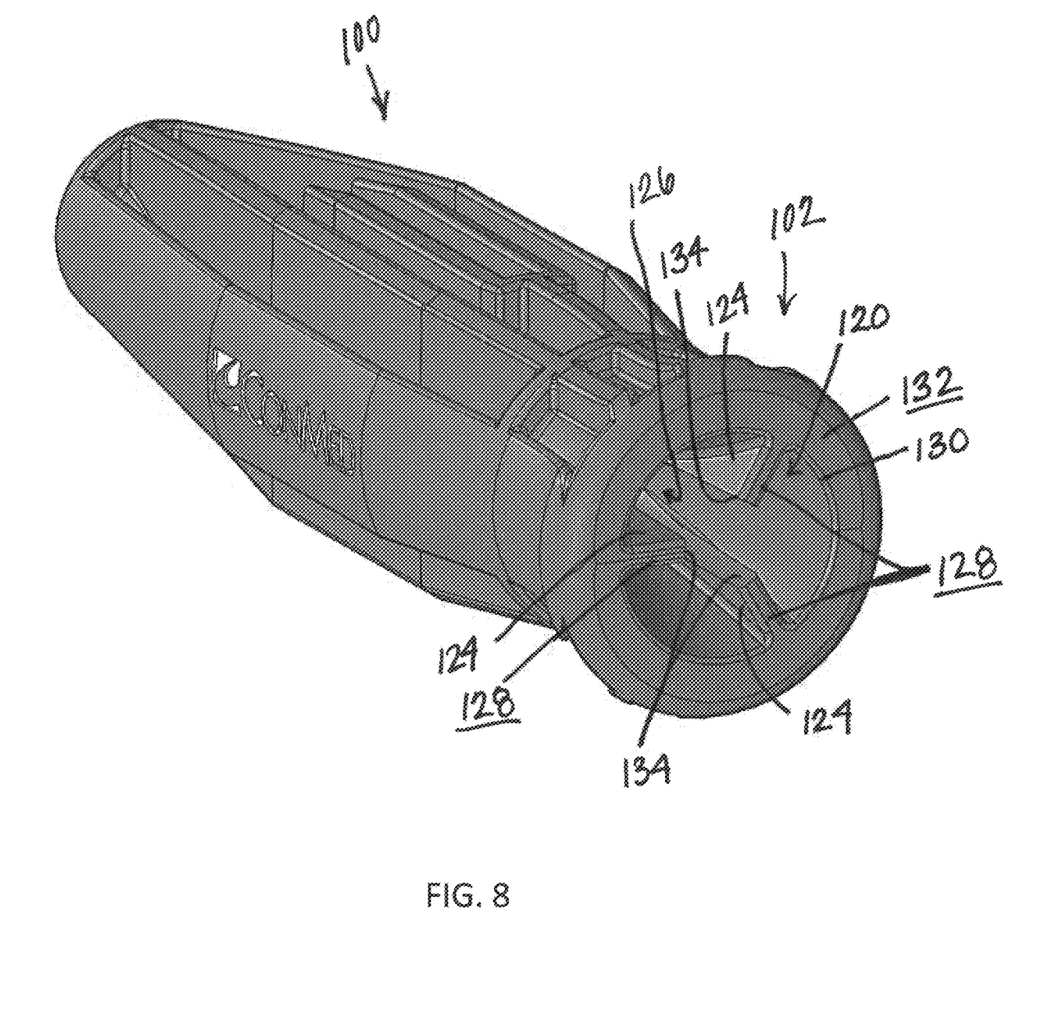
FIG. 8 is another perspective view schematic representation of the drill guide of FIG. 5.

Referring now to FIGS. 3 and 4, there are shown close-up perspective views schematic representations of the proximal end 102 of the drill guide 100. In the embodiment of the drill guide 100 shown in FIG. 3 (and FIG. 2), the fins 124 extending along the exterior surface 122 of the recess 120 extend to or connect to a proximal edge 130 of the recess 120. As shown in FIG. 3, each contact surface 128 of the fins 124 is substantially flush with or planar with a proximal surface 132 of the proximal end 102 of the drill guide 100.

FIG. 4 shows the proximal end 102 of the drill guide 100, according to an alternative embodiment. The fins 124 of the drill guide 100 in FIG. 4 do not extend to the proximal edge 130 of the recess 120. The fins 124 extend along the exterior surface 122 of the recess 120 between the proximal edge 130 and the channel 126. Because the fins 124 do not reach the proximal edge 130 of the recess 120, the drill guide 100 can accommodate an inserter 200 (FIGS. 12-15) with a large handle 202.

Referring now to FIGS. 5-8, there are shown various perspective views schematic representations of the drill guide 100, according to another embodiment. In the depicted embodiment, the contact surfaces 128 extend to the channel 126 in the drill guide 100. Similar to that shown in FIGS. 2-3, the contact surfaces 128 extend to the proximal edge 130 of the recess 120. In addition, the embodiment of the drill guide 100 shown in FIGS. 5-8 has contact surfaces 128 which are flush with the proximal surface 132 of the proximal end 102 of the drill guide 100. The funnel shape or taper of the recess 120 in FIGS. 5-8 is more gradual and deeper (i.e., extends farther distally) than the recess 120 of the drill guide 100 in FIGS. 1-4. The drill guide 100 in FIGS. 5-8 is optimized for injection molding. For example, the fins 124 in the recess 120 each have a central wall 134 which extend to the channel 126.

Figure 9:
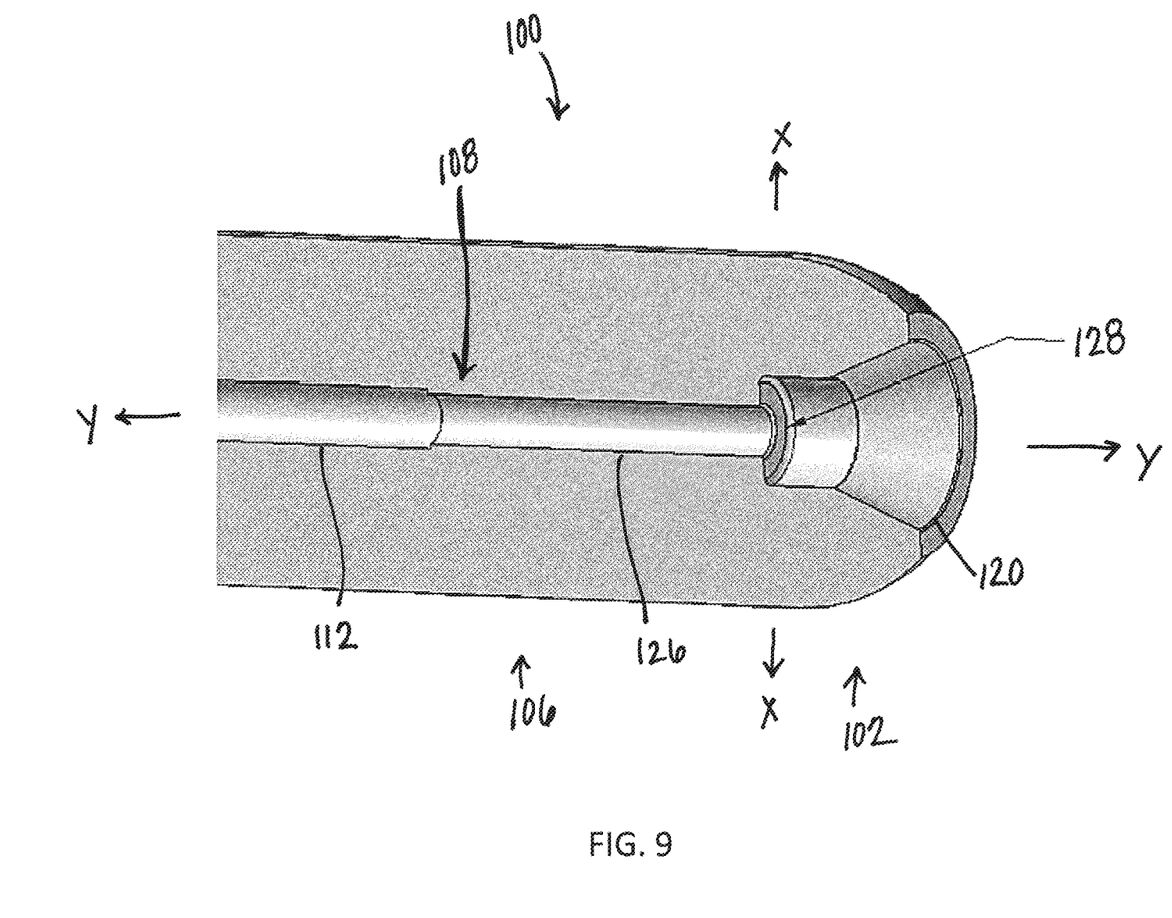
FIG. 9 is a partial sectional view schematic representation of the handle of the drill guide, according to an embodiment.

Turning now to FIG. 9, there is shown a partial sectional view schematic representation of the handle 106 at the proximal end 102 of the drill guide 100, according to an alternative embodiment. The drill guide 100 shown in FIG. 9 extends along a central longitudinal y-y axis. In the depicted embodiment, the recess 120 extending into the handle 106 is funnel-shaped, tapering distally along the central longitudinal y-y axis. The contact surface 128 within the recess 120 is a flat, distal surface in the recess 120. As shown in FIG. 9, the contact surface 128 extends along a lateral x-x axis which is substantially perpendicular to the central longitudinal axis y-y. In the depicted embodiment, the channel 126 in the recess 120 extends to the first portion 112 of the guide shaft 108 and the first portion 112 of the guide shaft 108 is within the handle 106.

Figure 10:
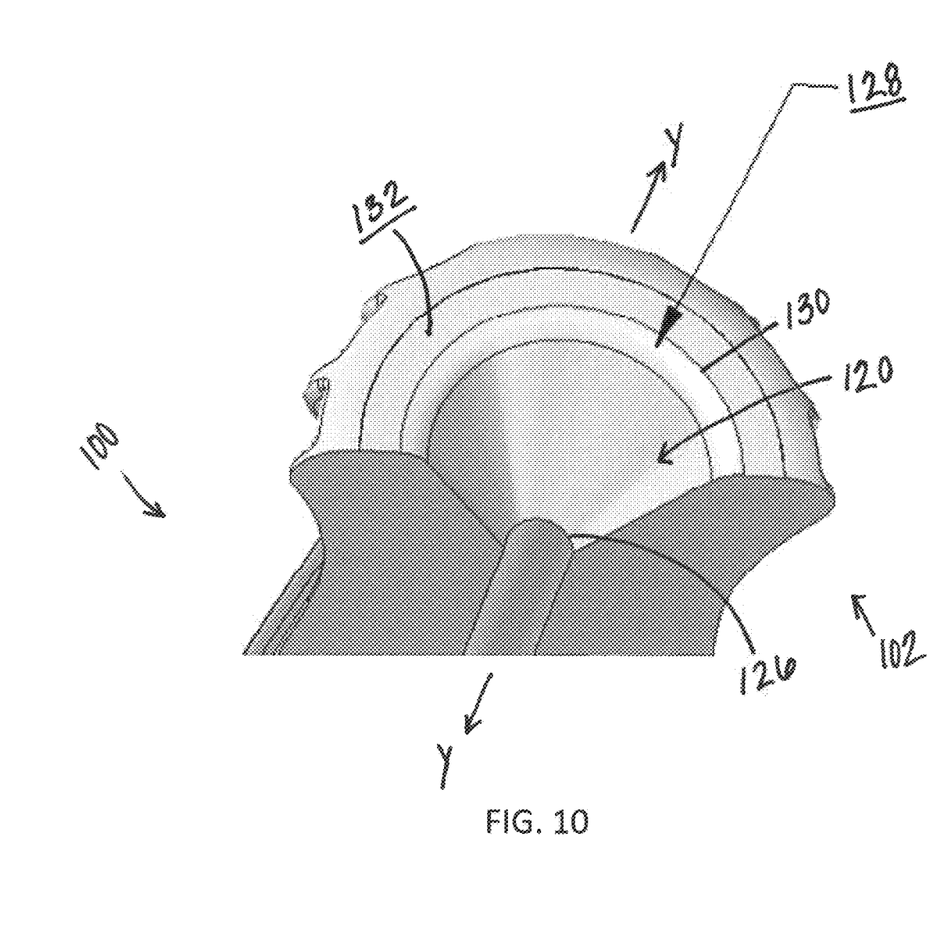
FIG. 10 is a close-up sectional view schematic representation of the proximal end of the drill guide, according to another embodiment.
Figure 11:
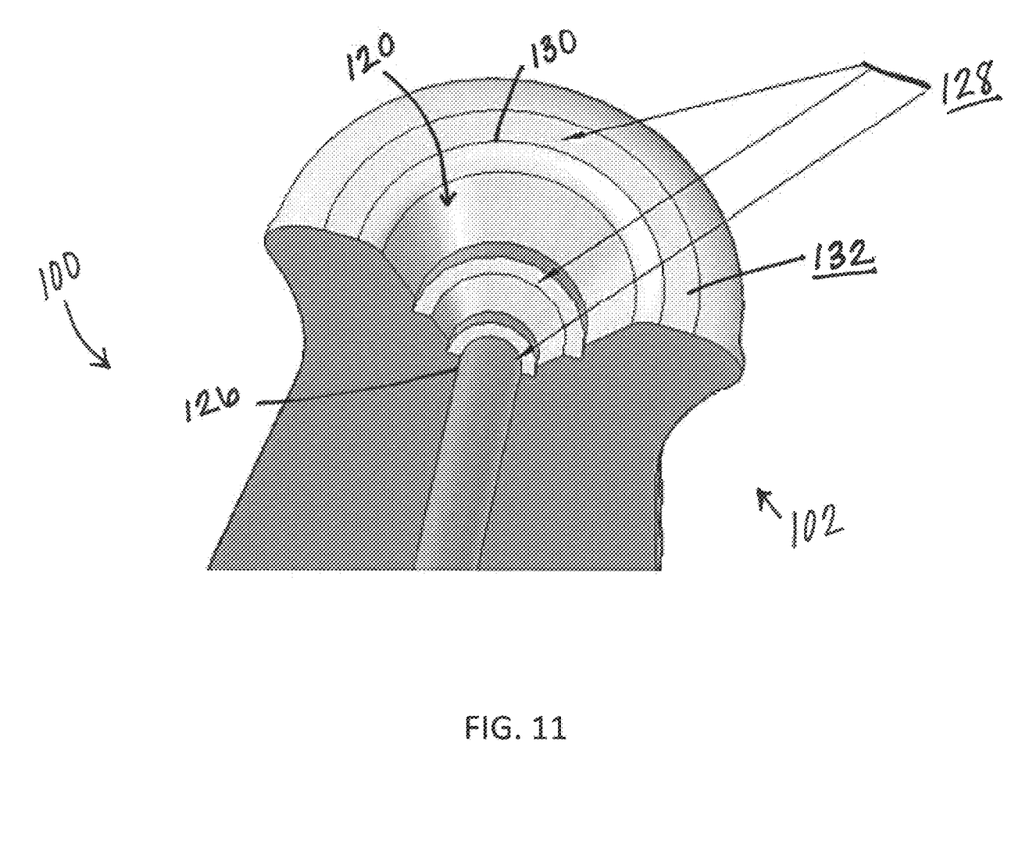
FIG. 11 is a close-up sectional view schematic representation of the proximal end of the drill guide, according to yet another embodiment.

Referring now to FIGS. 10-11, there are shown close-up sectional perspective views schematic representations of the proximal end 102 of the drill guide 100, according to another embodiment. In the depicted embodiment, the recess 120 extending into the handle 106 is also funnel-shaped, tapering distally. The drill guide 100 in FIG. 10 comprises a single ring-shaped contact surface 128. The contact surface 128 extends circumferentially within the recess 120. In the embodiment shown in FIG. 10, the contact surface 128 extends to the proximal edge 130 of the proximal end 102 of the drill guide 100. The contact surface 128 is also planar or substantially flush with the proximal surface 132 of the proximal end 102 of the drill guide 100. This reduces the risk that the tip of the inserter 200 (FIGS. 12-15) catches once it is in the recess 120 as the recess 120 is uninterrupted when following a line (e.g., central longitudinal y-y axis) into the channel 126.

The drill guide 100 in FIG. 11 comprises a plurality of ring-shaped contact surfaces 128. The contact surfaces 128 are spaced and extend circumferentially within the recess 120. In the embodiment shown in FIG. 11, one of the plurality of contact surfaces 128 extends to the proximal edge 130 of the proximal end 102 of the drill guide 100. That contact surface 128 is also planar or substantially flush with the proximal surface 132 of the proximal end 102 of the drill guide 100. As also shown in FIG. 11, another of the plurality of contact surfaces 128 extends from the channel 126. Stated differently, a contact surface 128 extends to and circumferentially around the channel 126. Having a plurality of contact surfaces 128 make the drill guide 100 compatible for multiple different inserters 200. The contact surfaces in FIG. 11 each have a width smaller than the width of the contact surface 128 of the drill guide 100 in FIG. 10. The contact surfaces 128 in FIG. 11 are smaller to reduce the likelihood that the tip of the inserter 200 (FIGS. 12-15) catches on the contact surfaces 128.

Figure 12:
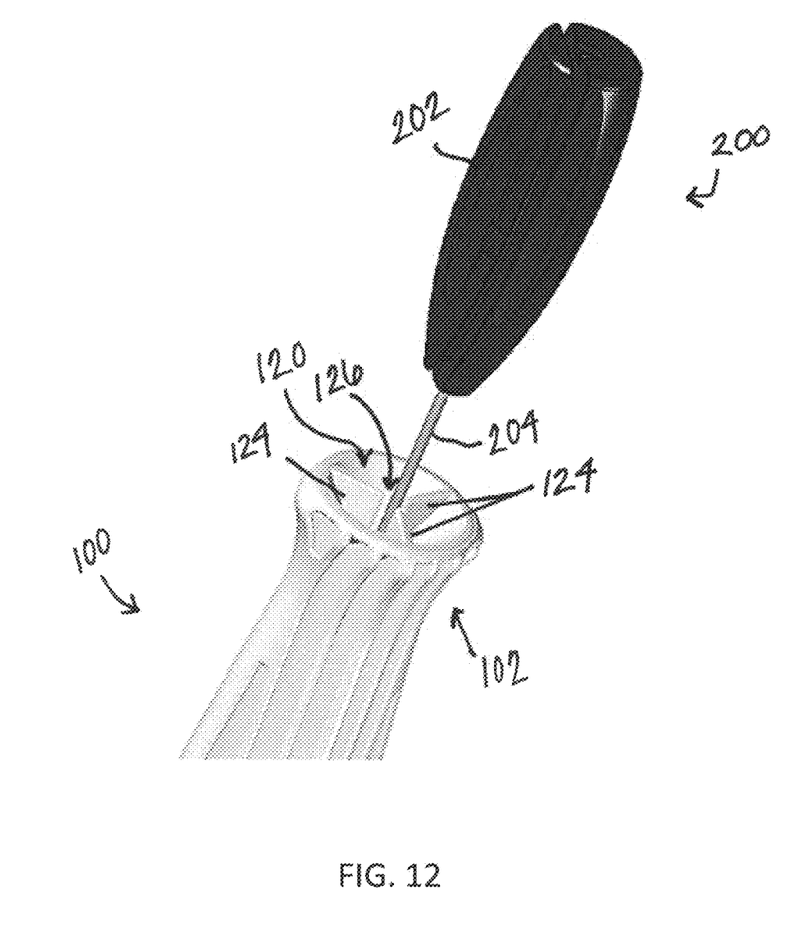
FIG. 12 is a perspective view schematic representation of a drill guide assembly in a first position, according to an embodiment.
Figure 14:
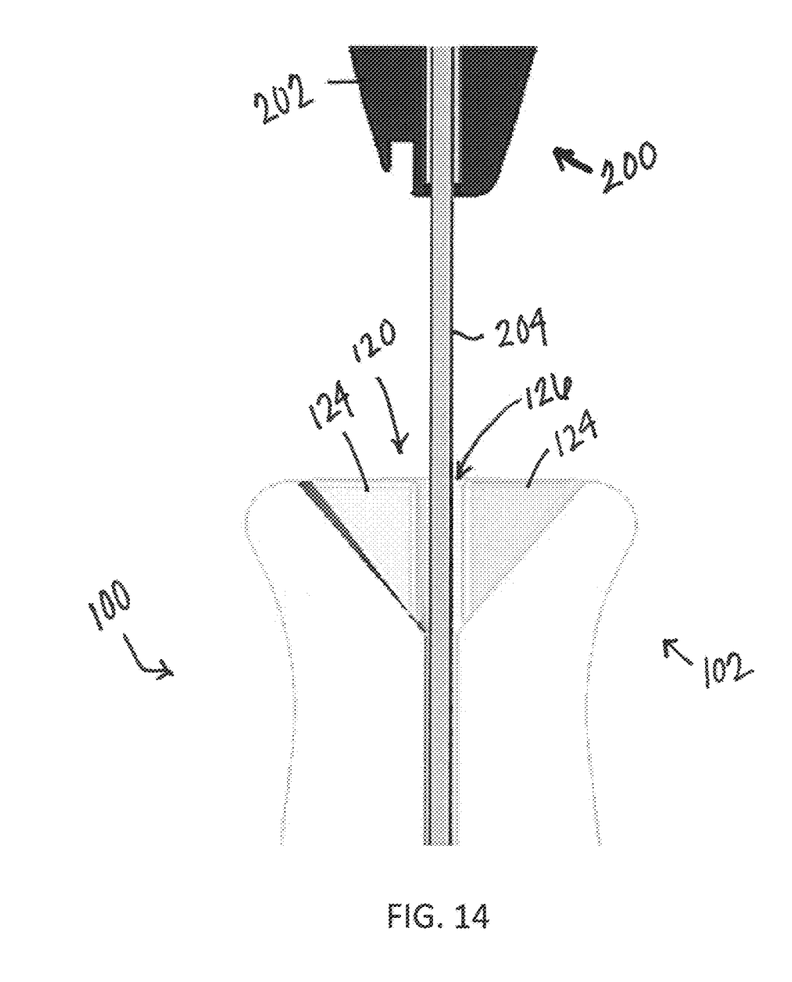
FIG. 14 is a side sectional view schematic representation of the drill guide assembly in the first position, according to an embodiment.

Turning now to FIGS. 12 and 14, there is shown a perspective view schematic representation and a side sectional view schematic representation, respectively, of a drill guide assembly 10 in a first position, according to an embodiment. The drill guide assembly 10 includes the drill guide 100 and the inserter 200. The inserter 200 includes a proximal handle 202 with a drive shaft 204 extending distally therefrom. The drive shaft 204 is sized and configured to fit within the channel 126 in the drill guide 100. In the first position, the drive shaft 204 of the inserter 200 enters the recess 120 between the fins 124. The channel 126 in the recess 120 then receives the drive shaft 204, as shown in FIGS. 12 and 14. From the first position, the inserter 200 is advanced within the channel 126 to a second position.

Figure 13:
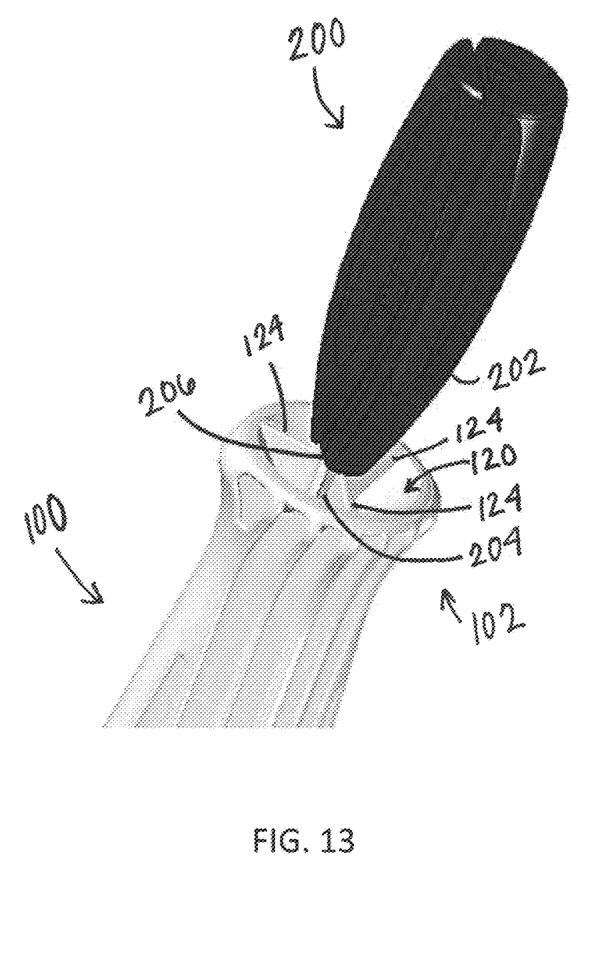
FIG. 13 is a perspective view schematic representation of the drill guide assembly of FIG. 12 in a second position.
Figure 15:
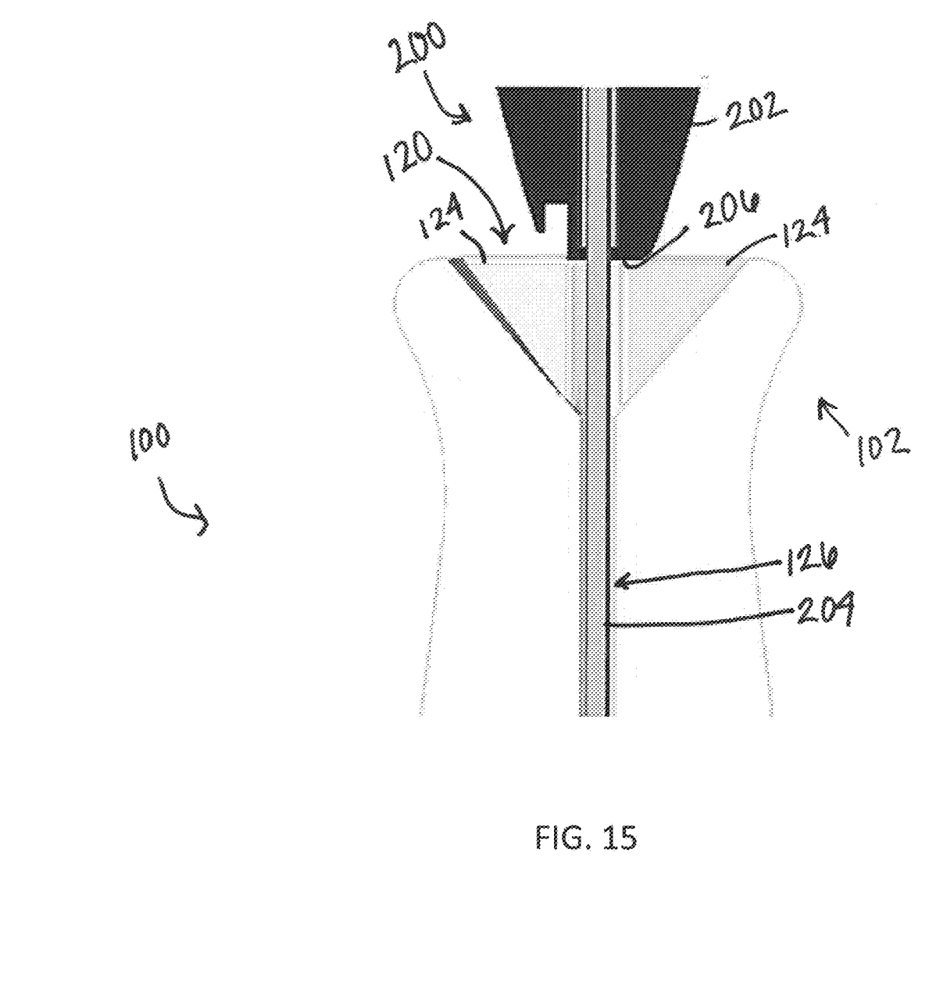
FIG. 15 is a side sectional view schematic representation of the drill guide assembly in the second position, according to an embodiment.

Referring now to FIGS. 13 and 15, there is shown a perspective view schematic representation and a side sectional view schematic representation, respectively, of a drill guide assembly 10 in a second position, according to an embodiment. To install an anchor (not shown) in a bone hole at the surgical site, the inserter 200 (with the anchor attached at its distal end) is advanced within the channel 126 and the guide shaft 108. The inserter 200 is advanced until it reaches the second position. In the second position, a distal end 206 of the handle 202 of the inserter 200 abuts the contact surface(s) 128 of the fins 124 in the recess 120 of the drill guide 100. Although not shown, in the second position, the anchor at the distal end of the inserter 200 extends from the distal crown end 116 (FIG. 1) of the drill guide 100.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A drill guide extending along a longitudinal axis with a proximal end and a distal end, the drill guide comprising:
   a handle extending from a distal end of the handle to the proximal end of the drill guide;

a guide shaft extending from the distal end of the handle to the distal end of the drill guide;
wherein the handle comprises a first diameter and the guide shaft comprises a second diameter, the first diameter being greater than the second diameter;
a recess extending into the handle at the proximal end of the drill guide;
a channel extending through the recess and into the guide shaft;
a contact surface extending from the recess;
a fin extending from an exterior surface of the recess, the fin having the contact surface thereon;
wherein the fin is substantially triangular;
wherein the fin extends from the channel to a proximal edge of the recess;
wherein the guide shaft extends to a distal crown end; and
wherein the distal crown end comprises a plurality of protrusions extending distally therefrom.

2. A drill guide extending along a longitudinal axis with a proximal end and a distal end, the drill guide comprising:
a handle extending from a distal end of the handle to the proximal end of the drill guide;
a guide shaft extending from the distal end of the handle to the distal end of the drill guide;
wherein the handle comprises a first diameter and the guide shaft comprises a second diameter, the first diameter being greater than the second diameter;
a recess extending into the handle at the proximal end of the drill guide;
a channel extending through the recess and into the guide shaft;
a plurality of protrusions extending from the recess, each protrusion having a proximal contact surface,
wherein the plurality of protrusions are substantially triangular;
wherein each of the plurality of protrusions extends from the channel to a proximal edge of the recess;
wherein the guide shaft extends to a distal crown end; and
wherein the distal crown end comprises a plurality of protrusions extending distally therefrom.

* * * * *